United States Patent
König et al.

(10) Patent No.: US 11,771,390 B2
(45) Date of Patent: Oct. 3, 2023

(54) METHOD AND DEVICE FOR DETERMINING THE CONTOUR OF ANATOMICAL STRUCTURES IN A DIGITAL X-RAY-BASED FLUOROSCOPIC IMAGE

(71) Applicant: Ziehm Imaging GmbH, Nuremberg (DE)

(72) Inventors: Thomas König, Nuremberg (DE); Klaus Hörndler, Nuremberg (DE); Jens Glasbrenner, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 228 days.

(21) Appl. No.: 17/074,408

(22) Filed: Oct. 19, 2020

(65) Prior Publication Data
US 2021/0137479 A1 May 13, 2021

(30) Foreign Application Priority Data
Nov. 7, 2019 (DE) ...................... 10 2019 007 747.4

(51) Int. Cl.
*A61B 6/00* (2006.01)
*G06T 7/11* (2017.01)

(52) U.S. Cl.
CPC .......... *A61B 6/5205* (2013.01); *A61B 6/4441* (2013.01); *A61B 6/461* (2013.01);
(Continued)

(58) Field of Classification Search
CPC ....... A61B 6/032; A61B 6/4441; A61B 6/461; A61B 6/481; A61B 6/487; A61B 6/504;
(Continued)

(56) References Cited

U.S. PATENT DOCUMENTS 5,056,524 A * 10/1991 Oe ........................ H04N 5/3205
378/98.12
8,774,363 B2 7/2014 Van Den et al.
(Continued)

OTHER PUBLICATIONS

Examination Report, Application No. 10 2019 007 747.4, dated Oct. 12, 2020.
(Continued)

*Primary Examiner* — Katrina R Fujita
(74) *Attorney, Agent, or Firm* — Knobbe, Martens, Olson & Bear LLP

(57) ABSTRACT

Medical imaging systems and methods for determining contours of anatomical structures of vessels and vessel sections for representation in X-ray-based fluoroscopic images. Methods can include capturing a mask image, recording at least one filling image including a vascular tree filled with contrast agent, subtracting the mask image from the at least one filling image to produce at least one vessel image, generating a segmented vessel image by segmenting the vascular tree filled with contrast agent in the at least one vessel image and removing from the at least one segmented vessel image such vessels and vessel sections that do not meet a threshold value, wherein the threshold value represents a function of at least one predetermined structural feature, and superimposing the at least one segmented vessel image with a live X-ray image and reproduction on a display device.

16 Claims, 2 Drawing Sheets

(52) U.S. Cl.
CPC ............... *A61B 6/504* (2013.01); *G06T 7/11* (2017.01); *G06T 2207/10121* (2013.01); *G06T 2207/10124* (2013.01); *G06T 2207/30104* (2013.01)

(58) Field of Classification Search
CPC ... A61B 6/5205; A61B 6/5235; A61B 6/5276; G06T 7/0014; G06T 7/11; G06T 7/136; G06T 2207/10121; G06T 2207/10124; G06T 2207/30101; G06T 2207/30104
See application file for complete search history.

(56) References Cited

U.S. PATENT DOCUMENTS

| | | | | |
|---|---|---|---|---|
| 2008/0080757 | A1* | 4/2008 | Scheuering | A61B 6/466 382/131 |
| 2012/0148139 | A1* | 6/2012 | Ozawa | A61B 6/504 382/132 |
| 2014/0294269 | A1* | 10/2014 | Mohr | G06T 7/155 382/131 |
| 2016/0051218 | A1* | 2/2016 | Oh | G06T 7/11 600/431 |
| 2018/0000441 | A1* | 1/2018 | Wang | A61B 5/004 |

OTHER PUBLICATIONS

S. Eiho, Y. Qian: Detection of coronary artery tree using morphological operator. In: Computers in Cardiology, 1997, 525-528.—ISSN 0276-6547.

N. Sulayman, M. Al-Mawaldi, Q. Kanafani: Semi-automatic detection and segmentation algorithm of saccular aneurysms in 2D cerebral DSA images. In: The Egyptian Journal of Radiology and Nuclear Medicine, 2016, 859-865.

* cited by examiner

METHOD AND DEVICE FOR DETERMINING THE CONTOUR OF ANATOMICAL STRUCTURES IN A DIGITAL X-RAY-BASED FLUOROSCOPIC IMAGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to medical imaging and more particularly to determination of contours of anatomical structures in x-ray-based fluoroscopic images.

Description of the Related Art

Numerous known medical engineering methods relate to the navigation of objects in the anatomy of a patient.

In such navigation of objects, for example when navigating catheters within vessels, X-ray imaging methods can be used to locate the object. The vessels themselves are initially not identifiable on the X-ray images (fluoroscopic images), which are generally continuously recorded. For this reason, a contrast agent, for example iodine dioxide or carbon dioxide, is administered to the patient—often repeatedly—which allows the vascular system to be made visible in the X-ray images.

The combined and/or simultaneous representation of the object, vascular system, and surrounding anatomy is very difficult, as will be shown below.

Repeated injection of contrast agent may be necessary, inter alia, since the contrast agent, for example iodine or carbon dioxide, dilutes rapidly in the blood stream, is then transported, for example, into the kidneys (iodine) or the lungs (carbon dioxide), and from there is excreted from the patient.

Methods for highlighting vascular structures are known from patent documents WO05055008 A2 and WO2010101660 A2. A method for the representation of vascular structures, which represents only one area of interest of the contour of the imaged vascular structures, is not disclosed. Furthermore, no method is disclosed which independently identifies an area of interest on the basis of the image content.

It may therefore be desirable to produce an improved representation of the contour of a vessel or vessel section.

SUMMARY

Embodiments of the present technology may improve the recognition, segmentation and representation of foreign objects in the representation of reconstructed volume data.

In some embodiments, a method may be used for determining contours of anatomical structures, in particular of vessels and vessel sections, for representation in a digital X-ray-based fluoroscopic image. The method includes capturing a mask image; recording at least one filling image including a vascular tree filled with contrast agent; subtracting the mask image from the at least one filling image to produce at least one vessel image; generating a segmented vessel image by segmenting the vascular tree filled with contrast agent in the at least one vessel image and removing from the at least one segmented vessel image such vessels and vascular sections that do not meet a threshold value, wherein the threshold value represents a function of at least one predetermined structural feature; and superimposing the at least one segmented vessel image with a live X-ray image and reproduction on a display device.

In some embodiments, an angiographic X-ray system for conducting the method includes an X-ray source, an X-ray detector, a computer with memory units, a control unit, a computer unit, at least one display device, a first image processing unit for generating the subtraction image from the mask image and the at least one filling image, which contains a vascular tree filled with contrast agent, a second image processing unit for segmenting the vascular tree filled with contrast agent in the at least one vessel image and for removing such vessels and vessel sections from the at least one vessel image that do not meet a threshold value, wherein the threshold value represents a function of at least one predetermined structural feature, a third image processing unit for extracting and superimposing a further X-ray image on a vascular tree filled with contrast agent, and a GUI with an input unit for the image processing units.

DETAILED DESCRIPTION

Figure 1:
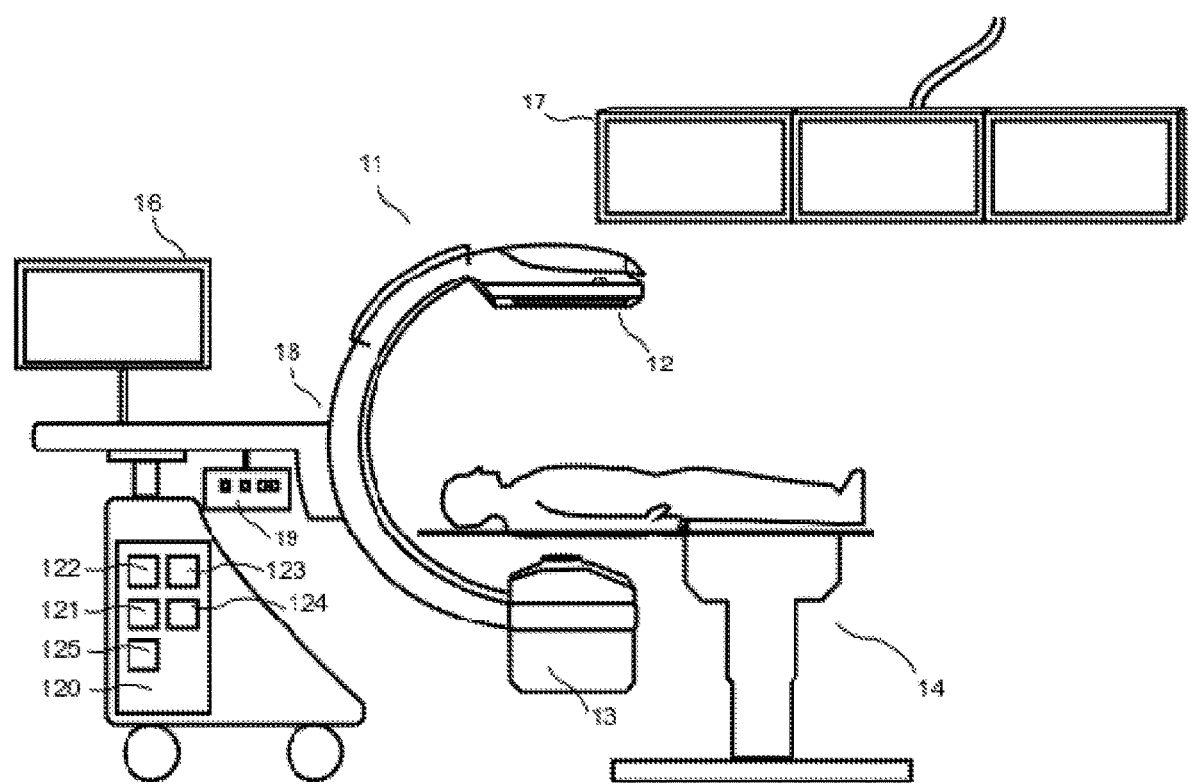
FIG. 1 illustrates a C-arm X-ray system that is suitable for carrying out the methods according to the present technology.

To address shortcomings of existing imaging methods, it may be desirable to generate a persistent representation of the vascular tree. In order to represent the vascular tree permanently, without a renewed addition of the contrast agent, a fluoroscopic image of the vascular tree and the anatomy surrounding it is first recorded without contrast agent (mask image). A contrast agent is then injected and X-ray images (filling images) are produced at different, successive points in time, which document the distribution of the contrast agent in the vessel at said different, successive points in time.

To represent just the vessel structures filled with contrast agent, the mask image is now subtracted (subtraction images) from a part of the filling images taken at different, successive points in time, so that only the vessels filled with contrast agent are represented as a temporal sequence (digital subtraction angiography; DSA). These X-ray images can then be combined to form an X-ray image which represents a vascular tree completely filled with contrast agent (vessel image). This can be done by a minimum method in which the lowest grayscale value for each pixel is converted from all subtraction images into the respective pixel of the vessel image over the course of time of the recording of the individual subtraction images.

A further representation can be produced by means of an inverted vessel image. In a roadmap method, this inverted vessel image (conditionally a first subtraction) can now be superimposed with a live DSA image (conditionally a second subtraction) and the navigation of an object in the anatomy of the patient can be simplified. This method thus represents the vascular tree previously extracted in the vessel image in light gray levels, but the catheter, which is visible in the DSA image, remains dark. As a result of the multiple subtractions involved, however, there is a sharp increase in the image noise and a deterioration of the dynamic range. In order to avoid this, alternatively, only the contours of the vessels can be superimposed with the X-ray live image. These contours can be extracted beforehand from the vessel image in a known way by means of image processing, for example via a threshold value formation of the gray levels and subsequent edge recognition.

In some embodiments of the present technology, a method may be used for determining contours of anatomical structures, in particular of vessels and vessel sections, for representation in a digital X-ray-based fluoroscopic image. The method includes capturing a mask image; recording at least one filling image including a vascular tree filled with contrast agent; subtracting the mask image from the at least one filling image to produce at least one vessel image; generating a segmented vessel image by segmenting the vascular tree filled with contrast agent in the at least one vessel image and removing from the at least one segmented vessel image such vessels and vascular sections that do not meet a threshold value, wherein the threshold value represents a function of at least one predetermined structural feature; and superimposing the at least one segmented vessel image with a live X-ray image and reproduction on a display device.

The recorded mask image can be a fluoroscopic image and represents the precontrast anatomy. The fluoroscopic image can also be obtained from the averaging of a plurality of recorded mask images. For recording the at least one filling image, a contrast agent can be used, for example iodine dioxide or carbon dioxide. By means of this, the otherwise invisible vessels, for example arteries and organs, can be made visible by means of X-rays.

During the passage of the contrast agent through the patient, X-ray images can be produced at different, successive points in time, which document the distribution of the contrast agent in the vessel at these different, successive points in time. For the representation of the vessels, at least one subtraction image is now formed from the at least one filling image and the mask image. These subtraction images can then be combined to form an X-ray image which represents a vascular tree completely filled with contrast agent (vessel image). This can take place, for example, by means of a minimum method, for example when iodine is used as contrast agent, or alternatively when a maximum method is used, for example when carbon dioxide is used, in which the respectively lowest (minimum method) or highest (maximum method) gray value for each pixel is converted from all X-ray images into the respective pixel of the filling image. Alternatively, a single DSA image can be used for this purpose. In this case, the minimum or maximum method is omitted.

Then, a segmented vessel image is produced by segmenting the vessel image, for example by a binary imaging operation, and the vessels and/or vascular segments which do not meet at least one threshold value are removed from the at least one segmented vessel image.

In this case, those regions which are not of interest during an intervention can be removed in a segmented vessel image. These uninteresting regions can, for example, be very small side vessels in the case of interventions on large vessels.

Furthermore, it is possible not to remove small vessels, if no large vessels are present in the image. In this case, the small vessels in particular are the areas of interest. Furthermore, regions of no interest can be removed, for example artifacts of movement during the contrast agent injection, which are erroneously recognized as vessels by the subtraction.

The at least one threshold value can be a function of a predetermined structural feature, for example a predetermined size (diameter, length, area) of a vessel or, for example, the grayscale value of a vessel or a combination of different structural features. Said at least one threshold value is preferably relatively rather than absolutely defined, so that the at least one threshold value criterion can be applied relative to the existing image information of the subtraction image.

Finally, the segmented at least one vessel image can be displayed on a display device with the X-ray live image, so that the vessels remain visible even without contrast agent administration.

One advantage of the present technology is the avoidance of the repeated injection of contrast agent during the placement of an instrument, for example a catheter, while taking into account a change in position.

Another advantage may be that the surrounding anatomy remains visible under the possible overlay of the contours on the X-ray live image and there is no reduction in the dynamic range as in the case of a roadmapping method.

A further advantage of the present technology can be the improved representation of the vessel contours and the limitation of these to an automatically identified region of interest.

The improved navigation of an object, for example a catheter in the vessel of interest, can also be advantageous, since, in contrast to classical navigation methods, poor visibility of the object, for example due to poor contrast, can be reduced.

An embodiment in which the vessel edges are extracted via edge detection in order to display only the vessel edges when superimposed with the live X-ray image, can be expedient.

Another advantage of the present technology can be the relative definition of the threshold value criterion as a function of the contents of the vessel image. In some embodiments, therefore, the dominant vessel diameter in the at least one vessel image can be used as a structural characteristic. In the 2D image, the vessel diameter is understood as the dimension of the vessel representation perpendicular to the center line of the vessel image. The dominant vessel diameter can be the diameter of the vessel which, in terms of area, represents the largest vessel and which does not exceed or does not fall below a predetermined ratio of length to diameter. Furthermore, for example, an average vessel diameter of all vessels shown in the at least one vessel image can be set as the dominant vessel diameter, the average vessel diameter being determined by the integration of all vessel diameters over the vessel length, divided by the total length of the vessels. In addition, instead of the average vessel diameter, for example, the median vessel diameter or another statistical measure (percentile) can be set as the dominant vessel diameter.

As an alternative, expedient embodiment, the largest vessel diameter can be used as a structural feature in the at least one vessel image.

In another embodiment, the present technology can also recognize contiguous vessel structures and remove such vessel structures which are not connected to the largest vessel in the visible region of the image. In this case, the largest vessel is preferably identified on the basis of the area which it occupies on the image, for example on the basis of the number of pixels occupied by the largest vessel.

An embodiment in which the segmentation takes place by means of binary image processing is expedient.

Another example embodiment can provide that the method includes recognizing and masking out such vessels and vessel sections or image regions recognized as ones whose area does not exceed a predetermined percentage of the area of the vessel or vessel section which is, for example, largest in terms of area, but which satisfy the predetermined structural feature. Said recognized image regions can correspond both to genuine vessels that are of no interest and to movement artifacts which appear during the subtraction of the mask image from the filling images.

Another example embodiment can provide that the method can extract the vessel edges and the vessels and vessel sections, specifically in such a way that the extracted vessels, vessel sections or vessel edges can be superimposed with a fluoroscopic image having an adaptive opacity.

In another embodiment, the extracted vessels, vessel sections or vessel edges can be superimposed in color with a fluoroscopy image. Both the real vessels that are of no interest and the movement artifacts can be identified as non-interesting vessels/areas. There is thus no differentiation between non-interesting vessels/regions and movement artifacts. Movement artifacts can appear as small islands, which can then be removed analogously to the small vascular islands. The criterion for the removal of non-interesting vessels/regions or movement artifacts can be the area of a non-interesting vessel/region if it is smaller than a given or predetermined threshold value, wherein the threshold value can depend on the dominant vessel diameter.

In an advantageous manner, the structural feature can be adjusted by an operator. This can take place before the execution of the method according to the present technology, or during the execution of the method, for example during the superimposing of the extracted edges of the vessels with an X-ray live image.

Another expedient embodiment can provide that the threshold value of the structural feature can be adjusted by an operator. This can likewise take place before the method according to the present technology is carried out, or during the execution of the method, for example during the superimposing.

In some embodiments, an angiographic X-ray system expediently contains a control unit for changing the structural feature and/or the threshold value. The angiographic X-ray system may be a modality from a group of modalities, wherein the group contains at least one X-ray diagnostic apparatus, C-arm X-ray apparatus, and a computer tomograph.

In some embodiments, a largely software-based implementation of the method has the advantage that even previously used methods can be retrofitted by means of a software update in order to operate according to the present technology. In this respect, the problem is also solved by a corresponding computer program product having a computer program which can be loaded directly into a memory device of a computer, for example a C-arm X-ray apparatus, having program sections in order to execute the methods according to the present technology when the computer program is executed by the computer. In addition to the computer program, such a computer program product may optionally comprise additional components such as documentation and/or additional components, including hardware components for using the software.

A computer-readable medium, for example a memory stick, a hard disk or another portable or permanently installed data carrier, on which are stored the program sections of the computer program which can be read and executed by a computer, can be used for transport to the control device and/or for storage on or in the control device. A connection to a network-connected hospital data system, radiology data system, or a global network in which are stored the program sections of the computer program, which can be read and executed by a computer, can also be used for the transport. The computer can have, for example, one or more cooperating microprocessors or the like for this purpose.

Referring now to the figures, a C-arm X-ray system 11, which is provided for realizing the disclosed methods for recording projection images of a scan, is shown schematically in FIG. 1.

The C-arm 18 carries an X-ray generator 13 at one end and an X-ray image detector 12 at the other end and opposite the X-ray generator 13. This X-ray image detector 12 can be a rectangular or square, flat semiconductor detector, for example made of amorphous silicon (a-Si). As an alternative, the use of, for example, counting CMOS detectors is likewise possible. The detector can also be a circular X-ray image intensifier. The C-arm 18 can preferably be adjusted by motor control in a plurality of axes in space, wherein the axes have sensors for detecting the extent of the adjustment.

In the beam path of the X-ray generator 13, a patient to be examined lies on a patient support table 14 as the object to be examined, for example for recording vascular structures.

The apparatus further includes a computer 120 having a memory unit 121, a control unit 123, an image processing unit 124, additional image processing units 122, and a network interface 125.

For example, the projections used for vessel representation can be stored or loaded into the memory unit 121. Said projections can either be loaded from a server or recorded by means of the C-arm X-ray system 11 before or during an intervention. An image processing unit 124 creates at least one subtraction image from the mask image 21 and the at least one filling image 23, which contains a vessel structure 25 filled with contrast agent. By means of additional image processing units 122, it is possible to implement image post-processing steps, for example edge smoothing, filtering, and sharpening.

Furthermore, the device contains a GUI with an image output unit 16 and an input unit 19, with which the threshold value and/or the structural feature can be changed by a user.

By means of the network interface 125, the recorded projections can be exchanged between the C-arm X-ray system 11 and, for example, a hospital data system, a radiology data system, and a global network.

There is also the possibility of additionally displaying projections and post-processed projections on further external display devices 17 by means of the network interface 125.

Figure 2:
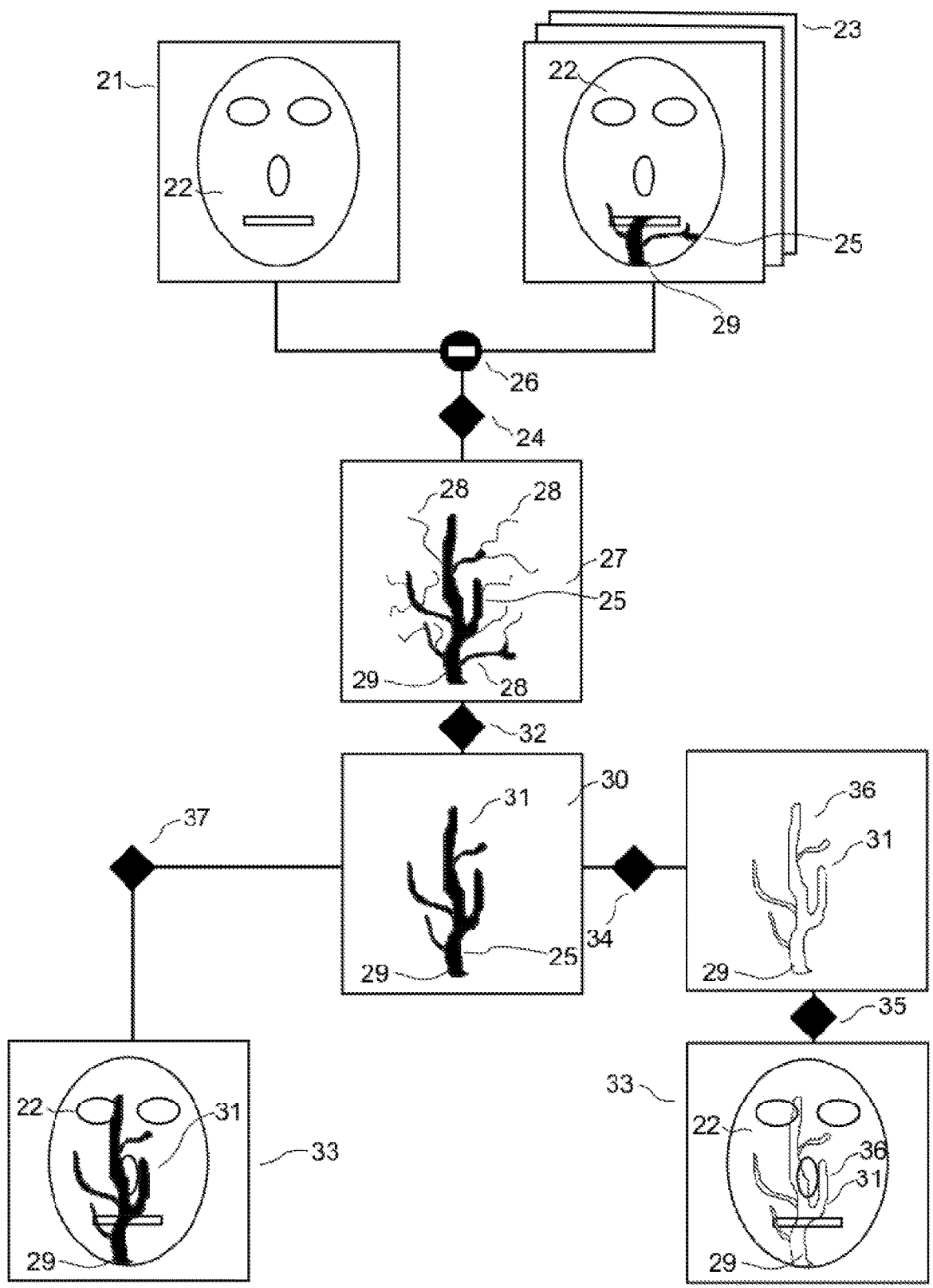
FIG. 2 illustrates an example embodiment of a method according to the present technology using the largest vessel diameter as threshold value criterion of the structural feature.

FIG. 2 shows one embodiment of a method in accordance with the present technology. In this case, a mask image 21 of a region to be examined, which shows only the pre-contrast anatomy 22, is first recorded. Next, a series of at least one filling image 23 is recorded, each image from the series of the at least one filling image 23 showing a vessel structure 25 filled or partially filled with contrast agent, wherein each image from a series of at least one filling image 23 represents a different state of filling of the vascular tree.

Following the creation of a series of at least one filling image 23, the mask image 21 is subtracted from said series of images of filling images 23 (subtraction step 26). A series of at least one subtraction image is produced, which show only the vessel structure 25 filled with contrast agent. Then, a vessel image 27 can be computed, for example by means of a minimum or maximum method 24, in which the respectively lowest or highest grayscale value for each pixel is converted from the images of the image series of the at least one subtraction image into the respective pixel of a vessel image 27.

According to the present technology, the vessel structure 25 filled with contrast agent is now segmented in the vessel image 27 resulting from the previous processing steps (segmentation step 32) and such vessels and vessel sections 28 which do not meet the threshold value criterion are removed from the segmented vessel image 30. According to the present technology, the structures of the vascular tree which meet the threshold criterion 31 can be retained. The determination that the dominant vessel diameter or the largest vessel diameter 29 or another characteristic diameter is the predetermined structural feature can be preset or can be made by a user before or during the use of the method according to the present technology. Furthermore, for a less obstructed image, organs are preferably also removed, for example a kidney which, although meeting the threshold value criterion of the predetermined structural feature "largest vessel diameter 29", can be recognized by the method according to the present technology as an organ. This can be done by the user. These can also be organs in the background which are not directly connected to the vascular structure filled with contrast agent in the foreground. This procedure can also be used on isolated vascular islands (not shown in the figure). These are recognized by the method according to the present technology as individual vessels and can be masked out by the method. This serves in particular for clarity and enables a better workflow.

Furthermore, the vessel contours 36 of the vessel structures 31 of the segmented vessel image 30 that meet the threshold value criterion can be extracted (extraction step 34) and then, for example, superimposed with the mask image 21 (superimposition step 35), preferably with an X-ray live image 33 of the pre-contrast anatomy 22 represented on the mask image 21, and displayed on a display device 16.

Alternatively, it is possible to superimpose the segmented vessel structures 31 satisfying the threshold value criterion directly (direct superimposition step 37) with the mask image 21, preferably with an X-ray live image 33 of the pre-contrast anatomy 22 shown on the mask image 21, and to display it on a display device 16.

LIST OF REFERENCE NUMERALS AND SYMBOLS

11 C-arm X-ray system
12 X-ray image detector
13 X-ray generator
14 Patient support table
16 Image output unit
17 External display devices
18 C-arm
19 Input unit
120 Computer
121 Memory unit
122 Additional image processing units
123 Control unit
124 Image processing unit
125 Network interface
21 Mask image
22 Pre-contrast anatomy
23 At least one filling image
24 Processing step: minimum or maximum
25 Vessel structure filled with contrast
26 Processing step: subtraction
27 Vessel image
28 Vessels and vessel sections
29 Largest vessel diameter
30 Segmented vessel image
31 Vessel structures satisfying threshold criterion
32 Processing step: segmentation
33 X-ray live image
34 Processing step: extraction
35 Processing step: superimposition
36 Vessel contours
37 Processing step: direct superimposition Other, particularly advantageous embodiments and further developments of the present technology shall become apparent from the dependent claims and the description, where in this case the independent claims of one category of claims can also be further developed analogously to the dependent claims of another category of claims; and, in particular, individual features of different exemplary embodiments or variants can be combined to form new exemplary embodiments or variants.

What is claimed is:

1. A method for determining contours of anatomical structures of vessels and vessel sections for representation in an X-ray-based fluoroscopic image, the method comprising:
    capturing a mask image;
    recording at least one filling image including a vascular tree filled with contrast agent;
    subtracting the mask image from the at least one filling image to produce at least one vessel image;
    generating a segmented vessel image by segmenting the vascular tree filled with contrast agent in the at least one vessel image and removing from the at least one segmented vessel image such vessels and vessel sections having one or more dimensions smaller than a threshold value, wherein the threshold value is defined relative to at least one predetermined structural feature comprising a dominant vessel diameter or a largest vessel diameter in the at least one vessel image; and
    superimposing the at least one segmented vessel image with a live X-ray image and reproduction on a display device,
    wherein the definition of the threshold value relative to the at least one structural feature is adjustable by an operator to change a number of vessels and vessel sections displayed in the segmented vessel image.

2. The method of claim 1, wherein the predetermined structural feature is a dominant vessel diameter in the at least one vessel image.

3. The method of claim 1, wherein the predetermined structural feature is a largest vessel diameter in the at least one vessel image.

4. The method of claim 1, further comprising extracting vessel edges of the segmented vessel image via edge detection such that, when the at least one segmented vessel image is superimposed with the X-ray live image, only the vessel edges of the vessels are displayed.

5. The method of claim 1, wherein connected vessel structures are recognized.

6. The method of claim 1, wherein the segmentation and removal of vessels and vessel sections takes place by means of binary image processing.

7. The method of claim 1, wherein such vessels and vessel sections whose area does not exceed a predetermined percentage of an area of the largest vessel or vessel section, but which meet the predetermined structural feature, are detected and masked.

8. The method of claim 1, wherein the extracted vessels, vessel sections or vessel edges are superimposed with a fluoroscopy image having an adaptive opacity.

9. The method of claim 1, wherein the extracted vessels, vessel sections or vessel edges are superimposed in color with a fluoroscopic image.

10. The method of claim 1, wherein the predetermined structural feature can be adjusted by an operator.

11. The method of claim 1, wherein the threshold value of the structural feature can be adjusted by an operator.

12. A device having an angiographic X-ray system for carrying out the method of claim 1, the device comprising:
- an X-ray source;
- an X-ray detector;
- a computer with memory units;
- a control unit;
- a computer unit;
- at least one display device;
- a first image processing unit for generating the subtraction image from the mask image and the at least one filling image, which contains a vascular tree filled with contrast agent;
- a second image processing unit for segmenting the vascular tree filled with contrast agent in the at least one vessel image and for removing such vessels and vessel sections from the at least one vessel image having one or more dimensions smaller than a threshold value, wherein the threshold value is defined relative to at least one predetermined structural feature comprising a dominant vessel diameter or a largest vessel diameter in the at least one vessel image;
- means for adjusting the definition of the threshold value relative to the at least one structural feature to change a number of vessels and vessel sections displayed in the segmented vessel image;
- a third image processing unit for extracting and superimposing a further X-ray image on a vascular tree filled with contrast agent; and
- a GUI with an input unit for the image processing units.

13. The device of claim 12, wherein the control unit has means for changing the structural feature.

14. The device of claim 12, wherein the angiographic X-ray system is a modality from a group of modalities, wherein the group contains at least one C-arm X-ray apparatus, an X-ray diagnostic apparatus, and a CT scanner.

15. A tangible, non-transitory, computer-readable storage medium having stored thereon a computer program which can be loaded directly into a memory unit of a computer of an angiographic X-ray system, in particular a C-arm X-ray device, with program sections that cause the angiographic X-ray system to perform the method according to claim 1 when the computer program is executed in the computer of the angiographic X-ray system.

16. A tangible, non-transitory, computer-readable storage medium having stored thereon program sections which can be read and executed by a computer unit in order to perform the method according to claim 1 when the program sections are executed by the computer unit.

* * * * *